United States Patent [19]
Henke et al.

[11] Patent Number: 5,869,447
[45] Date of Patent: Feb. 9, 1999

[54] CYCLOHEXAPEPTIDES AND THEIR MIXTURES, A PROCESS FOR PREPARING THEM, AND THEIR USE

[75] Inventors: Stephan Henke, Hofheim; Birgit Jordan, Hattersheim; Jochen Knolle, Kriftel; Leander Lauffer, Gladenbach; Susanne Feiertag, Tübingen; Karl-Heinz Wiesmüller, Tübingen; Günther Jung, Tübingen, all of Germany

[73] Assignee: Hoechst Aktiengesellschaft, Frankfurt am Main, Germany

[21] Appl. No.: 571,797

[22] Filed: Dec. 13, 1995

[30] Foreign Application Priority Data

Dec. 13, 1994 [DE] Germany ............... 44 44 260.2

[51] Int. Cl.$^6$ .................................. A61K 38/00
[52] U.S. Cl. ................. 514/9; 514/11; 530/317; 530/321; 436/501; 436/503
[58] Field of Search .................. 530/317, 321; 514/9, 11; 436/501, 503

[56] References Cited

U.S. PATENT DOCUMENTS 4,659,691  4/1987  Veber et al. ............... 514/11

FOREIGN PATENT DOCUMENTS

| 0 519 640 | 12/1992 | European Pat. Off. . |
| 0578083 | 12/1994 | European Pat. Off. . |
| 2360562 | 3/1978 | France . |
| 4322330 | 3/1994 | Germany . |
| 1530560 | 11/1978 | United Kingdom . |
| WO 92/00091 | 1/1992 | WIPO . |
| WO 95/01800 | 1/1995 | WIPO . |

OTHER PUBLICATIONS

Else et al., "Helper T–cell Subsets in Mouse Trichuriasis," *Parasitology Today*, vol. 7, No. 11 (1991), pp. 313–316.

Cox, "Parasites and Human T–cell Subsets," *Parasitology Today*, vol. 7, No. 10 (1991), p. 261.

Mosmann et al., "Diversity of Cytokine Synthesis and Function of Mouse CD4+ T Cells," *Immunological Reviews*, No. 123 (1991), pp. 209–229.

Romagnani, "Human TH1 and TH2 subsets: doubt no more," *Immunology Today*, vol. 12, No. 8 (1991), pp. 256–257.

Kapsenberg et al., "Functional subsets of allergen–reactive human CD4+ T cells," *Immunology Today*, vol. 12, No. 11 (1991), pp. 392–395.

Bell, "'Uncommon' Amino Acids in Plants," *FEBS Letters*, vol. 64, No. 1 (1976), pp. 29–35.

Gray, "Data for Biochemical Research," 2nd Ed., (1969), pp. 1–65.

*Practical Handbook of Biochemistry and Molecular Biology* (1989), pp. 3–69.

Ma et al., Biopolymers, 34(8), 987–1000, 1994.

*Primary Examiner*—Cecilia J. Tsang
*Assistant Examiner*—C. Delacroix-Muirheid
*Attorney, Agent, or Firm*—Finnegan, Henderson, Farabow, Garrett & Dunner, L.L.P.

[57] ABSTRACT

The invention relates to compounds of the formula I cyclo(A-B-C-E-F-(D)-Ala)  (I)

in which

A, B, C, E and F are each independently the residue of a natural amino acid other than cysteine (Cys) and tryptophan (Trp), their mixtures and their physiologically tolerated salts; to a process for their preparation and to their use for preparing a diagnostic agent, a medicament for the treatment or prophylaxis of allergies and infections, or a scientific tool for inhibiting the binding of interleukin-4 (IL-4) to the IL-4 receptor.

27 Claims, 6 Drawing Sheets

CYCLOHEXAPEPTIDES AND THEIR MIXTURES, A PROCESS FOR PREPARING THEM, AND THEIR USE

The invention relates to compounds of the formula I cyclo(A-B-C-E-F-(D)-Ala)     (I)

in which

A, B, C, E and F are each independently the residue of a natural amino acid other than cysteine (Cys) and tryptophan (Trp), i.e., alanine (Ala), arginine (Arg), asparagine (Asn), aspartic acid (Asp), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tyrosine (Tyr) or valine (Val), or the physiologically tolerated salts thereof.

Preferred compounds of the formula I are those in which A and B are each independently Ile, Leu, Val, Phe or Tyr, and C, D, and F are each independently the residue of a natural amino acid other than cysteine and tryptophan.

Particularly preferred compounds of the formula I have the following peptide sequences:

cyclo(Val-Val-Xaa-Val-Val-(D)-Ala);

cyclo(Val-Tyr-Xaa-Val-Tyr-(D)-Ala); or cyclo(Tyr-Val-Xaa-Tyr-Val-(D)-Ala), where Xaa is the residue of a natural amino acid other than Cys and Trp.

Natural amino acids are understood to mean all α-amino acids, as described, for example, in Bell, *FEBS Letters*, 64, pp. 29–35 (1976), which is herein incorporated by reference. These amino acids occur naturally in the free state or as structural units of proteins. In the case of the amino acids which occur naturally as the structural units of proteins, natural amino acids are understood to mean L-amino acids (with the exception of glycine). (D)-Ala therefore corresponds to the residue of the amino acid alanine in the D configuration.

Peptides are understood to mean a sequence of amino acids which are linked to each other by peptide bonds, with the peptides having an N-terminus and a C-terminus. The amino acid sequences enclosed by brackets describe cyclopeptides in which the N-terminus (the amino group) of the first amino acid is linked to the C terminus (of the COOH group) of the last amino acid.

Physiologically tolerated salts of compounds of the formula (I) are understood to mean both inorganic and organic salts, as described, for example, in *Remington's Pharmaceutical Sciences*, 17th ed. (1985), the relevant portions of which, such as p. 1418, are herein incorporated by reference. Illustrative examples of suitable salts include, but are not limited to, alkali metal and alkaline earth metal salts, salts with physiologically tolerated amines, and salts with inorganic or organic acids such as HCl, HBr, $H_2SO_4$, maleic acid or fumaric acid.

The above described compounds of the formula (I) are cyclohexapeptides which can be synthesized according to the generally known methods which are customary in peptide chemistry. For example, the inventive cyclohexapeptides may be synthesized by:

a) coupling suitably protected amino acid derivatives to a solid support;

b) cleaving-off the linear peptide while retaining the side-chain protective groups;

c) cyclizing the peptide in solution; and d) eliminating the side-chain protective groups.

Suitable amino acid protective groups are any of the protective groups known to those skilled in the art, such as those described in T. W. Greene and P. G. M. Wuts, *Protective Groups in Organic Synthesis* (1991), which is incorporated herein by reference. Illustrative protective groups include those which are customarily used in peptide synthesis, such as those described in *Kontakte Merck* 3/79, pp. 14–22 and 1/80, pp. 23–35, the relevant portions of which are herein incorporated by reference.

Illustrative examples of urethane groups for protecting amino functions include, but are not limited to, Pyoc, Fmoc, Fcboc, Z, Boc, Ddz, Bpoc, Z-($NO_2$), Dobz, Moc, Mboc, Iboc, Adoc, Adpoc, Msc or Pioc. These amino acid protective groups may be removed using acids, bases or reductively.

Illustrative examples of groups for protecting a guanidino group include $NO_2$, tosyl, Boc, Z, mesitylene-2-sulfonyl (Mts) and the like. These groups may be eliminated hydrolytically or hydrogenolytically.

The COOH side-chain functions are preferably blocked as alkyl esters, preferably methyl, ethyl or tert-butyl esters, or as benzyl esters or modified benzyl esters (p-$NO_2$, p-Cl, p-Br inter alia). These moieties may be deblocked by alkaline or acidic hydrolysis or by hydrogenation.

Illustrative examples of hydroxyl protective groups include tert-butyl and benzyl. These protective groups may be removed by any of the suitable methods known to those skilled in the art.

The present invention further relates to mixtures of the cyclohexapeptides of the formula (I). It is possible to synthesize the above-mentioned cyclohexapeptides in the form of mixtures using so-called "combinatorial synthesis techniques". PCT Application WO 92/000091, which is incorporated herein by reference, discloses combinatorial synthesis techniques which can be used to synthesize "peptide libraries" in a simple manner.

Mixtures of the compounds of the formula I can be prepared in accordance with the above-listed steps a)–d). However, if combinatorial synthesis techniques are used it is not necessary to individually synthesize all $18^5$ possible cyclohexapeptides of the formula I. Rather, a mixture of cyclohexapeptides of the formula I may be prepared by simultaneously adding all 18 different amino acids for each synthesis cycle. An advantage of this technique as compared with conventional synthesis methods is apparent, i.e., peptide mixtures which contain all possible cyclohexapeptides of the formula I are obtained after running through the synthesis cycle only 5 times, with all the desired amino acids being used simultaneously on each occasion, and then cyclizing with only one synthesis.

However, as an alternative to the method which has just been described, mixtures of the amino acids do not need to be added in all the synthesis cycles. For example, after one synthesis cycle, the support material on which the peptide mixtures were synthesized can be fractionated and a desired amino acid can be inserted at a particular position in subsequent, separate synthesis reactions.

After peptide mixtures have been prepared using the above described methods, any peptides possessing biological activity must be detected and their sequences must be identified. This can be done by using an iterative resynthesis method which is explained below using as an example a mixture which contains the cyclopeptides of the formula A.

cyclo($O_1$-$O_2$-Xaa-Xaa-Xaa-(D)-Ala)     (A)

This mixture contains cyclohexapeptides having three variable positions (Xaa) which are occupied by all natural amino acids, other than Cys or Trp. The remaining positions are occupied by defined amino acids (O) (these are likewise natural amino acids other than Cys and Trp). One position is always D-Ala.

A mixture of the cyclopeptides A can be prepared as described above by carrying out 3 synthesis cycles using a mixture of all 18 amino acids and then fractionating the support material, with the peptide mixtures bound to it, and then preparing cyclopeptide mixtures of the formula A in 324 (18×18) separate syntheses. Each of these 324 mixtures in turn contains approximately 5800 ($18^3$) different peptides.

Each of the 324 mixtures which is found to be active in a bioassay (see below) is selected out and restricted in its complexity by iterative resynthesis involving the fresh insertion of a further defined position. Each phase of an iterative resynthesis requires 18 new synthesis steps. The effects of the cyclohexapeptides of defined structure which are finally obtained are confirmed by testing in a bioassay. The following scheme clarifies the procedure which has just been described. Peptide having three defined positions:

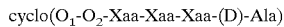

1. Specific bioassay (324 tests)
2. Identification of the active mixture
3. Syntheses (18) of peptides having 4 defined positions
Peptide having four defined positions:

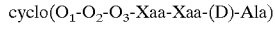

1. Specific bioassay (18 tests)
2. Identification of the active mixture
3. Syntheses (18) of peptides having 5 defined positions
Peptide having five defined positions:

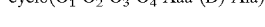

1. Specific bioassay (18 tests)
2. Identification of the active mixture
3. Syntheses (18) of peptides having 6 defined positions
Peptide having six defined positions:

1. Specific bioassay (18 tests)
2. Identification of the active peptide

In principle, the mixtures of the cyclopeptides can also be fractionated or purified by conventional analytical methods such as preparative HPLC or other chromatographic methods.

It has now been found that cyclohexapeptides of the formula I, or mixtures thereof, specifically inhibit the binding of interleukin-4 (IL) to the IL-4 receptor and suppress IL-4 activity. Consequently, the novel substances are effective inhibitors of IL-4 activity.

The IL-4-inhibiting effect of the novel compounds, or of their mixtures, can be measured in cell-free binding assays or in cellular bioassays.

German Patent Application DE 43 22 330 A1, which is incorporated herein by reference, discloses that suppression of IL-4 activity can be used to diagnose, provide therapy for and/or treat diseases which are associated with an increased appearance of T helper cells of the TH2 type.

The therapy and prophylaxis of many allergic, viral, parasitic and bacterial diseases still represents a major problem. It is known that changes in subpopulations of lymphocytic and monocytic cells take place during the course of some parasitic, viral and bacterial diseases. This is the case, for example, as regards the increased appearance of so-called type 2 T helper cells (termed TH2 cells in that which follows). In a general manner, T cells can be subdivided into subpopulations on the basis of surface markers and on the basis of their function. Thus, T helper lymphocytes, for example, carry CD4 surface molecules and, after having been activated, secrete cytokines.

Analyses of the cytokine pattern of cloned T helper cells from healthy mice, or from mice stimulated with allogenic cells, have shown that these helper cells produce interleukin-2, interleukin-4, gamma interferon, interleukin-5, interleukin-6, interleukin-10 and lymphotoxin (T helper cells of the so-called ThO type).

Following the cloning of T helper cells from mice which had been infected, for example, with the bacterial antigen Brucella abortus or with Mycobacterium tuberculosis, most clones were found to secrete lymphotoxin, gamma interferon and interleukin-2 but little or no interleukin-4, interleukin-5, interleukin-6 or interleukin-10 (T helper cells of the so-called TH1 type).

When T helper cells were cloned which were derived, for example, from susceptible mice which had been infected with parasitic pathogens such as Leishmania major, most of the clones which appeared produced increased quantities of interleukin-4, interleukin-5 and interleukin-10, but reduced, or non-detectable, quantities of interleukin-2 and gamma interferon (T helper cells of the TH2 type) (Mosmann et al., *Immunological Review*, 123, pp. 209–229 (1991) and S. Romagnani, *Immunology Today*, 12(8), pp. 256–257 (1991), which are each incorporated herein by reference).

This increased appearance of TH2 lymphocytes has already been detected in some infectious diseases of animals and humans (Else and Grenic, *Parasitology Today*, 7(11), pp. 313–316 (1991) and *Parasitology Today*, 7(10), p. 261 (1991), which are each incorporated herein by reference) and is also reflected in secondary parameters. For example, mice infected with Leishmania major generally had a reduced production of gamma interferon, a strongly elevated serum IgE and eosinophilia.

In general, strongly elevated concentrations of IgE were found in the sera of human patients suffering, for example, from lepromatous leprosy, leishmaniasis or schistosomiasis or infected with Mycobacteriumtuberculosis as compared with the concentrations found in the sera of healthy persons. In the case of the parasitic infections, an eosinophilia is often observed in the course of the disease.

A dysregulation of this type is also a feature of IgE mediated allergic reactions of the immediate type such as atopic dermatitis and asthma. For example, antigenspecific T cell clones from skin biopsies from patients suffering from atopic dermatitis are in the main of the TH2 type (Kapsenberg et al., *Immunology Today*, 12(11), pp. 392–395 (1991), which is incorporated herein by reference).

The novel compounds and mixtures are suitable both for the therapy and prophylaxis and for the diagnosis of allergies and infections, in particular viral, bacterial and parasitic infections and also fungal infections; preferably infections with human immunodeficiency virus (HIV), mycobacteria in particular Mycobacterium leprae, with listerias, with protozoa, especially the genera Leishmania and Plasmodium, with helminths, especially the genera Schistosoma, Nippostrongylus and Heligmosomoides, with Trichurida, Trichinella, Taenia (Cysticercus), Candida and Aspergillus. However, allergic reactions of the immediate type, in particular IgE-mediated reactions can also be diagnosed, treated or prophylactically treated. These include, in particular, atopic dermatitis and asthma.

In general, the administration forms differ in different diseases. For example, topical administration can be advantageous in some diseases. For example, administration by inhalation is advantageous in the case of asthma, while administration in the form of eye drops is advantageous in the case of conjunctivitis and dermal or intradermal administration is advantageous in the case of atopic dermatitis, since the pathological TH2 cells can, in particular, be detected topically.

The novel peptides, or their mixtures, can also be employed generally as scientific tools for inhibiting the binding of interleukin-4 (IL-4) to IL-4 receptors.

The invention furthermore relates to pharmaceutical preparations which contain compounds of the formula I or their mixtures. The medicaments may, for example, be used in the form of pharmaceutical preparations which can be administered orally, for example in the form of tablets, coated tablets, hard or soft gelatin capsules, solutions, emulsions or suspensions. The inclusion of the medicaments in liposomes, which may, where appropriate, contain further components such as proteins, likewise represents a suitable administration form. They may also be administered rectally, for example in the form of suppositories, or parenterally, for example in the form of injection solutions.

For the production of pharmaceutical preparations, these compounds can be worked into therapeutically inert organic and inorganic excipients. Illustrative examples of such excipients for tablets, coated tablets and hard gelatin capsules include lactose, corn starch or derivatives thereof, tallow and stearic acid or salts thereof.

Suitable excipients for the preparation of solutions include water, polyols, sucrose, invert sugar and glucose. Suitable excipients for injection solutions include water, alcohols, polyols, glycerol and vegetable oils. Suitable excipients for suppositories include vegetable and hardened oils, waxes, fats and semiliquid polyols.

The pharmaceutical preparations may also contain preservatives, solvents, stabilizers, wetting agents, emulsifiers, sweeteners, dyes, flavorants, salts for altering the osmotic pressure, buffers, coating agents, antioxidants, and/or other therapeutic active compounds where appropriate.

The invention also relates to a process for preparing a novel medicament, which comprises bringing at least one compound of the formula (I), together with a pharmaceutically suitable and physiologically tolerated excipient and, where appropriate, further suitable active compounds, additives or auxiliary substances, into a suitable form for administration.

Preferred administration forms are oral and topical administrations, local administrations, for example using a catheter, or else injections.

Experimental section:

The following (preparation) examples are intended to explain the invention in more detail without there being any desire to limit the breadth of the invention in any way. The following abbreviations were used:

| Abbreviations: | |
|---|---|
| AA | amino acid |
| BSA | bovine serum albumin |
| TLC | thin layer chromatography |
| DCM | dichloromethane |
| DIC | diisopropylcarbodiimide |
| DIPEA | diisopropylethylamine |
| DMF | dimethylformamide |
| DMSO | dimethyl sulfoxide |
| ELISA | enzyme-linked immunosorbent assay |

-continued

| Abbreviations: | |
|---|---|
| Fmoc | 9-fluorenylmethyloxycarbonyl |
| HOBt | 1-hydroxybenzotriazole |
| HPLC | high pressure (performance) liquid chromatography |
| huIL | human interleukin |
| IL | interleukin |
| muIL | murine interleukin |
| PBS | phosphate-buffeted saline |
| PBSA | bovine serum albumin in PBS |
| TBTU | benzotriazolyltetramethyluronium tetrafluoroborate |
| TFA | trifluoroacetic acid |

Competitive huIL-4 binding test

▲ huIL-4, ● K0021, ■ K0022, ◆ K5933

Figure 1:
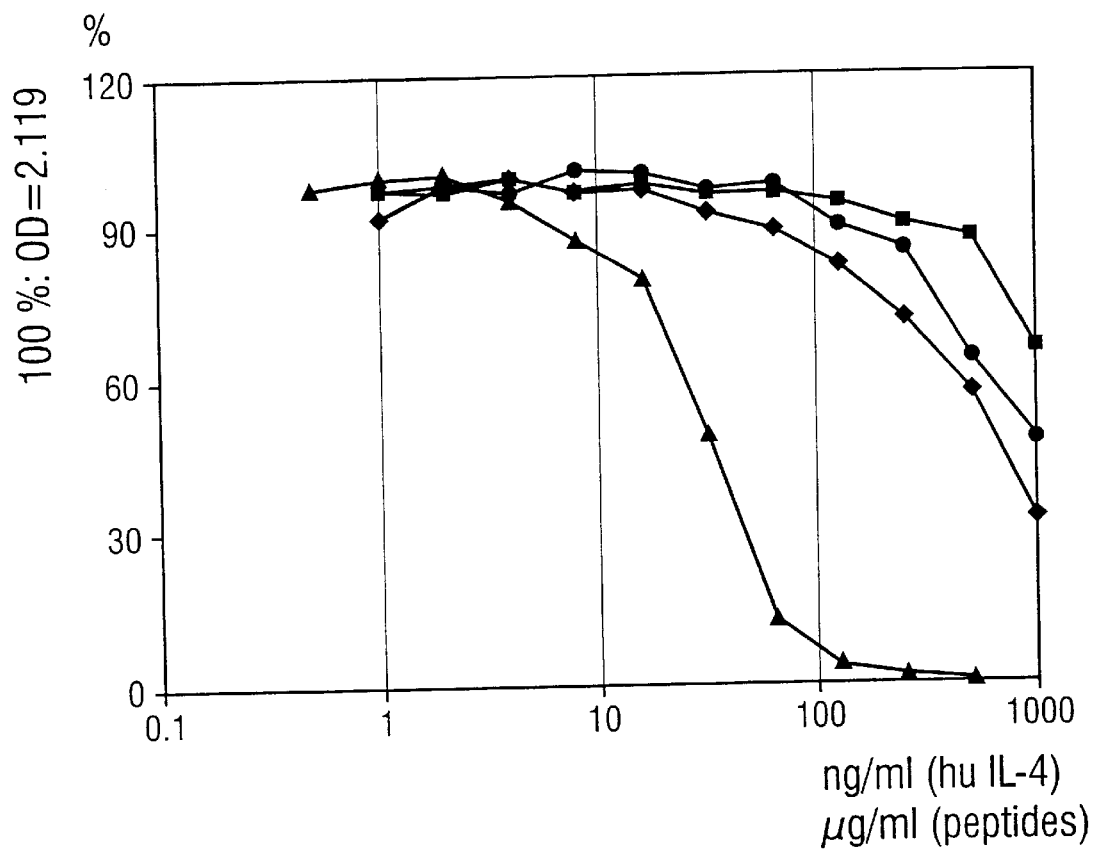
FIG. 1.

FIG. 2:

Competitive muIL-4 binding test

▲ muIL-4, ● K0021, ■ K0022, ◆ K5933

FIG. 3:

Competitive huIL-1ra test

▲ huIL-1ra, ● K0021, ■ K0022, ◆ K5933

FIG. 4:

Testing the peptides in a huIL-4-dependent bioassay a) Standard curve huIL-4 (titrated), ■ huIL-4 b) Addition of peptides (titrated) to 1 ng/ml huIL-4 (constant)

X K5993, ◆ K0021, ▲ K0022

FIG. 5:

Testing the peptides in an muIL-4-dependent bioassay a) Standard curve muIL-4 (titrated), ■ muIL-4 b) Addition of peptides (titrated) to 1 ng/ml muIL-4

X K5933, ◆ K0021, ▲ K0022

FIG. 6:

Testing the peptides in a huIL-1 beta-dependent bioassay a) Standard curve huIL-1 beta (titrated), ■ huIL-1 b) Addition of peptides (titrated) to 0.5 U/ml huIL-1 beta (constant)

x K5933, ◆ K0021, ▲ K0022

SYNTHESIS OF THE CYCLOHEXAPEPTIDES

The described cyclopeptides are prepared as individual peptides or in a mixture. The synthesis is carried out by:

a) coupling suitably protected amino acid derivatives to a solid support;

b) cleaving-off the linear peptide while retaining the side-chain protective groups;

c) cyclizing the peptide in solution; and d) eliminating the side-chain protective groups.

Step a) Synthesis of the linear peptides or peptide mixtures: 13.1 g of Fmoc-D-Ala-Trityl resin was suspended in 131 ml of dichloromethane/dimethylformamide (DCM/DMF) (2:1), and 0.4 ml (40 mg, 0.032 mmol) of the resin suspension was, in each case, pipetted into the prepared reaction vessels. The reaction vessels were Eppendorf tips which were plugged with glass wool and inserted into the synthesis blocks of an apparatus for automated multiple peptide synthesis. 0.7M solutions of the necessary Fmoc amino acids were added, with the coupling being carried out with a 5-fold excess of Fmoc amino acid following in-situ activation with diisopropylcarbodiimide (DIC), which was added in 5-fold excess as a 1.5M solution in DMF/DCM (1:2). The coupling time was 50 min.

Defined peptide mixtures were obtained by mixing the supports (polymeric beads) which were coated with individual peptides.

Protocol of the synthesis cycle on an automated SYRO synthesizer:

| Operation | Reagent/solvent | Vol. [µl] | Time |
|---|---|---|---|
| 1. Swelling | DMF | 400 | 2 × 1 min |
| 2. Deblocking | 40% piperidine/DMF | 250 | 1 × 15 min |
| 3. Washing | DMF | 400 | 7 × 0.8 min |
| 4. Coupling | Fmoc.AA/HOBT (0.7M) DIC (1.7M) | 220 100 | 50 min |
| 5. Washing | DMF | 230/250/300 | 3 × 0.8 min |

Step b) Cleaving the linear peptides or peptide mixtures from the resin:

The peptides or peptide mixtures were cleaved from the resin (1 g in each case) in so-called Falcons® with 30 ml of acetic acid/methanol/DCM (2:2:6) at room temperature for 3 h while shaking. The resins were filtered off from the cleavage solution and the solvents were removed at 300 mbar/40° C. (DCM/methanol) or 1 mbar/40° C. (acetic acid) in a vacuum concentrator. The residues were dissolved in tert-butyl alcohol/water (4:1), and 2 eq. of 0.2N HCl (based on the amino groups) were added to this solution, which was concentrated once again in a vacuum concentrator.

Step c) Cyclization of the linear peptides or peptide mixtures:

0.4 mmol volumes of a peptide or a peptide mixture were dissolved in 250 ml of DMF (0.0016M) in polypropyiene flasks, and 4 eq. of diisopropylethylamine (DIPEA) were added. 3 ml of a 0.4M HOBt/TBTU solution in DMF (3 eq., 1.2 mmol) were slowly added dropwise in each case while shaking. The course of the reaction was monitored by TLC, and the reaction was terminated after 5 h. The solvents were removed at 1 mbar/40° C. overnight (15 h) in a vacuum concentrator, and the dry residues were taken up in DCM; these solutions were extracted by shaking with 5% $KHSO_4$, 5% $NaHCO_3$ solutions and water (3× in each case). The organic phases were dried over $Na_2SO_4$, filtered and concentrated in vacuo. The residues were dissolved in tertbutyl alcohol/water (4:1), and these solutions were lyophilized.

Step d) Elimination of the side-chain protective groups:

In each case, 100–200 mg of the cyclopeptide or the cyclopeptide mixture were treated with 5 or 10 ml, respectively, of elimination solution (TFA/thioanisole/thiocresol, 0.95:0.25:0.25) at room temperature for 4 h in order to eliminate the side-chain protective groups. The cyclopeptides were then precipitated in diethyl ether/n-heptane (1:1), centrifuged, washed a further two times with diethyl ether/n-heptane and dissolved in tertbutyl alcohol/water (4:1). These solutions were freeze-dried.

EXAMPLE 1

Synthesis of cyclo(Val-Tyr-Xaa-Val-Tyr-(D)-Ala) (K0021)

a) Synthesis of the linear peptide mixture:

(Val-Tyr-Xaa-Val-Tyr-(D)-Ala)

In order to synthesize the linear peptide mixture (Val-Tyr-Xaa-Val-Tyr-(D)-Ala) comprising 18 components (Val-Tyr-Ala-Val-Tyr-(D)-Ala; Val-Tyr-Arg-Val-Tyr-(D)-Ala; Val-Tyr-Asn-Val-Tyr-(D)-Ala; Val-Tyr-Asp-Val-Tyr-(D)-Ala; Val-Tyr-Gln-Val-Tyr-(D)-Ala; Val-Tyr-Glu-Val-Tyr-(D)-Ala; Val-Tyr-Gly-Val-Tyr-(D)-Ala; Val-Tyr-His-Val-Tyr-(D)-Ala; Val-Tyr-Ile-Val-Tyr-(D)-Ala; Val-Tyr-Leu-Val-Tyr-(D)-Ala; Val-Tyr-Lys-Val-Tyr-(D)-Ala; Val-Tyr-Met-Val-Tyr-(D)-Ala; Val-Tyr-Phe-Val-Tyr-(D)-Ala; Val-Tyr-Pro-Val-Tyr-(D)-Ala; Val-Tyr-Ser-Val-Tyr-(D)-Ala; Val-Tyr-Thr-Val-Tyr-(D)-Ala; Val-Tyr-Tyr-Val-Tyr-(D)-Ala; Val-Tyr-Val-Val-Tyr-(D)-Ala), these individual peptides were synthesized on polymeric supports using a robot designed for multiple peptide synthesis. As reaction vessels, polypropylene filtration columns were in each case filled with 40 mg (0.032 mmol) of Fmoc-D-Ala-2-chlorotrityl resin. The resin quantities were apportioned either by weighing in the dry resin or by pipetting a resin suspension in dichloromethane/dimethylformamide (2:1). 0.7M solutions of the necessary Fmoc amino acids together with equimolar quantities of N-hydroxybenzotriazole (HOBt) in dimethylformamide (DMF) were added, and the coupling was carried out using a 5-fold excess of Fmoc amino acids by in-situ activation with DIC, which was added, in 5-fold excess, as a 1.5M solution in dichloromethane/dimethylformamide (2:1). The coupling time was 50 min.

b) Cleaving the linear peptide mixture from the resin:

Prior to cleaving the peptides from the resin, 18 individual hexapeptide resins were pooled (18×40 mg-0.72 g of peptide resin) to give the peptide mixture (Val-Tyr-Xaa-Val-Tyr-(D)-Ala). The peptide mixture comprising a total of 0.72 g of peptide resin was cleaved, at room temperature for 3 h and while shaking, with 20 ml of acetic acid/methanol/dichloromethane (2:2:6). The resin was filtered off from the cleavage solution and the solvent was removed in a rotary vacuum concentrator (BetaRVC, Christ, Osterode) at 200 mbar/40° C. (DCM/methanol) or 1 mbar/40° C. (acetic acid). The residue was dissolved in tert-butyl alcohol/water (4:1), 2 eq. of 0.2N HCl (based on the amino group) were added and the whole was concentrated to dryness in a rotary vacuum concentrator.

c) cyclization:

Peptide mixture (Val-Tyr-Xaa-Val-Tyr-(D)-Ala) (0.4 mmol) was dissolved in 250 ml of DMF (0.0016M) in a polypropylene flask and 4 eq. of diisopropylethylamine (DIPEA) were added; the mixture was then cooled for 1 h in a freezer. 3 ml of a 0.4M HOBt/TBTU/DMF solution (~3 eq., 1.2 mmol) were slowly added dropwise while shaking. The course of the reaction was monitored by thin layer chromatography (mobile phase: chloroform/methanol/glacial acetic 85:15:2, $R_f$ Product=0.59). The reaction was complete after 3 h. The solvent was removed at 1 mbar/40° C. in a rotary vacuum concentrator and the dry residue was dissolved in dichloromethane; this solution was extracted by shaking with 5% KHSO4 solution and water. The organic phase was dried over $Na_2SO_4$. The solvent was evaporated off in vacuo and the residue was dissolved in tert-butyl alcohol/water (4:1) and this solution was lyophilized.

d) elimination of the side-chain protective groups:

Cyclopeptide mixture (Val-Tyr-Xaa-Val-Tyr-(D)-Ala) (100–200 mg) was treated, at room temperature for 4 h, with 10 ml of elimination solution (TFA/thioanisole/thiocresol, 0.95:0.025:0.025) in order to eliminate the side-chain protective groups. The elimination solution was added, while stirring slowly, to diethyl ether/n-heptane (1:1), the precipitate was centrifuged off and the sediment was washed twice with diethyl ether/n-heptane by ultrasonicating it and dissolved in tert-butyl alcohol/water (4:1); this solution was then freeze-dried.

e) analysis of the cyclopeptide mixture:

The cyclopeptide mixture was analyzed by HPLC and ion spray mass spectroscopy. MS (FAB): cyclo(Val-Tyr-Xaa-Val Tyr-(D)-Ala);
Xaa=Gly: 653.8 (M+H); Xaa=Ala; 667.8(M+H); Xaa=Ser: 683.8 (M+H); Xaa=Pro: 693.9 (M+H); Xaa=Val: 695.9 (M+H); Xaa=Thr: 697.9 (M+H); Xaa=Leu: 709.9 (M+H); Xaa=Ile: 709.9 (M+H); Xaa=Asn: 710.9 (M+H); Xaa=Asp: 711.8 (M+H); Xaa=Lys: 724.9 (M+H); Xaa=Gln: 724.9 (M+H); Xaa=Glu: 725.9 (M+H); Xaa=Met: 728 (M+H); Xaa=His: 733.9 (M+H); Xaa=Phe: 743.9 (M+H); Xaa=Arg: 752.9 (M+H); Xaa=Tyr: 759.9 (M+H).

EXAMPLE 2

Synthesis of cyclo(Val-Val-Xaa-Val-Val-(D)-Ala) (K 5993)

The cyclopeptide mixture cyclo (Val-Val-Xaa-Val-Val-(D)-Ala) was synthesized in an analogous manner to that employed in Example 1 using the appropriate amino acids. MS (FAB): cyclo(Val-Val-Xaa-Val-Val-(D)-Ala);
Xaa=Gly: 525.7 (M+H); Xaa=Ala: 539.7 (M+H); Xaa=Ser: 555.7 (M+H); Xaa=Pro: 565.8 (M+H); Xaa=Val: 567.8 (M+H); Xaa=Thr: 569.8 (M+H); Xaa=Leu: 581.8 (M+H); Xaa=Ile: 581.8 (M+H); Xaa=Asn: 582.8 (M+H); Xaa=Asp: 583.7 (M+H); Xaa=Lys: 596.8 (M+H); Xaa=Gln: 596.8 (M+H); Xaa=Glu: 597.8 (M+H); Xaa=Met: 599.9 (M+H); Xaa=His: 605.8 (M+H); Xaa=Phe: 615.8 (M+H); Xaa=Arg: 624.8 (M+H); Xaa=Tyr: 631.8 (M+H).

EXAMPLE 3

Synthesis of cyclo(Tyr-Val-Xaa-Tyr-Val-(D)-Ala) (K 0022)

Cyclopeptide mixture cyclo(Tyr-Val-Xaa-Tyr-Val-(D)-Ala) was synthesized in an analogous manner to that employed in Example I using the appropriate amino acids. MS (FAB): cyclo(Tyr-Val-Xaa-Tyr-Val-(D)-Ala);
Xaa=Gly: 653.8 (M+H); Xaa=Ala: 667.8 (M+H); Xaa=Ser: 683.8 (M+H); Xaa=Pro: 693.9 (M+H); Xaa=Val: 695.9 (M+H); Xaa=Thr: 697.9 (M+H); Xaa=Leu: 709.9 (M+H); Xaa=Ile: 709.9 (M+H); Xaa=Asn: 710.9 (M+H); Xaa=Asp: 711.8 (M+H); Xaa=Lys: 724.9 (M+H); Xaa=Gln: 724.9 (M+H); Xaa=Glu: 725.9 (M+H); Xaa=Met: 728 (M+H); Xaa=His: 733.9 (M+H); Xaa=Phe: 743.9 (M+H); Xaa=Arg: 752.9 (M+H); Xaa=Tyr: 759.9 (M+H).

EXAMPLE 4

The following cyclopeptides or cyclopeptide mixtures were prepared in an analogous manner.
cyclo(Val-Tyr-Ala-Val-Tyr-(D)-Ala);
cyclo(Tyr-Val-Ala-Tyr-Val-(D)-Ala);
cyclo(Tyr-Val-Hyp-Tyr-Val-(D)-Ala);
cyclo(Tyr-Val-Ala-Gly-Xaa-(D)-Ala);
cyclo(Tyr-Val-Ala-Gln-Xaa-(D)-Ala);
cyclo(Tyr-Val-Ala-Lys-Xaa-(D)-Ala);
cyclo(Tyr-Val-Ala-Asn-Xaa-(D)-Ala);
cyclo(Tyr-Val-Ala-Ile-Xaa-(D)-Ala);
cyclo(Tyr-Val-Ala-Leu-Xaa-(D)-Ala);
cyclo(Tyr-Val-Ala-Pro-Xaa-(D)-Ala);
cyclo(Tyr-Val-Ala-Phe-Xaa-(D)-Ala);
cyclo(Tyr-Val-Ala-His-Xaa-(D)-Ala);
cyclo(Tyr-Val-Ala-Ala-Xaa-(D)-Ala);
cyclo(Tyr-Val-Ala-Tyr-Xaa-(D)-Ala);
cyclo(Tyr-Val-Gln-Tyr-Val-(D)-Ala);
cyclo(Tyr-Val-Lys-Tyr-Val-(D)-Ala);
cyclo(Tyr-Val-Glu-Tyr-Val-(D)-Ala);
cyclo(Tyr-Val-Asp-Tyr-Val-(D)-Ala);
cyclo(Tyr-Val-Phe-Tyr-Val-(D)-Ala);
cyclo(Tyr-Val-Gly-Tyr-Val-(D)-Ala);
cyclo(Tyr-Val-His-Tyr-Val-(D)-Ala);
cyclo(Tyr-Val-Ile-Tyr-Val-(D)-Ala);
cyclo(Tyr-Val-Leu-Tyr-Val-(D)-Ala);
cyclo(Tyr-Val-Asn-Tyr-Val-(D)-Ala);
cyclo(Tyr-Val-Pro-Tyr-Val-(D)-Ala);
cyclo(Tyr-Val-Arg-Tyr-Val-(D)-Ala);
cyclo(Tyr-Val-Ser-Tyr-Val-(D)-Ala);
cyclo(Tyr-Val-Thr-Tyr-Val-(D)-Ala);
cyclo(Tyr-Val-Val-Tyr-Val-(D)-Ala);
cyclo(Tyr-Val-Tyr-Tyr-Val-(D)-Ala); and
cyclo(Tyr-Val-Met-Tyr-Val-(D)-Ala);
Hyp is hydroxyproline.

Measurement of the Biological Activity in Bioassays

EXAMPLE 5

Specific inhibition of IL-4 Binding in Cell-free Binding Assays.

EP 488 170 A1, which is incorporated herein by reference, discloses cell-free binding tests. For carrying them out, recombinant chimeric proteins were used which comprise the extracellular region of what are normally membrane-located receptors on to whose carboxyl terminus has been fused the Fc region of a heavy immunoglobulin chain composed of hinge, CH2 and CH3 domains. These so-called receptor/Fc fusion proteins can be bound, while retaining the specific receptor binding activity, to solid phases which have previously been coated, for example, with monoclonal antibodies directed against the Fc moiety. For this example, Nunc® type B ELISA plates were used as the solid phase. Receptor/Fc fusion proteins, dissolved in PBS containing 10 mg/ml BSA (PBSA), were bonded to these pre-treated plates (huIL-4R/Fc: 500 ng/ml; muIL-4R/Fc: 250 ng/ml; huIL-1R/Fc: 125 ng/ml; at room temperature for 1 h). After washing, the peptides or the respective specific unlabeled ligands (huIL-4R/Fc: huIL-4; muIL-4R/Fc: muIL-4; huIL-1R/Fc: huIL-Ira) were added in varying concentrations, followed by the specific ligands in biotinylated form, which were added at a fixed concentration (100 ng/ml). The plates were incubated at room temperature for 1 h in PBSA containing 5% DMSO. After having been washed, the plates were incubated at room temperature for 20 min with streptavidin/peroxidase (Amersham, 1:2000 in PBSA). The bound peroxidase was detected after the plates had been washed repeatedly in a solution of tetramethylbenzidine substrate (Behringwerke). The extinction at 450 nm, which directly reflects the quantity of the biotinylated ligand bound to the receptor, was measured after the plates had been incubated for 30 min. For FIGS. 1–3, the measured extinction signal was plotted against the concentration of the competing agent with the 100% value being the extinction which was measured in the absence of any competing agent.

Figure 2:
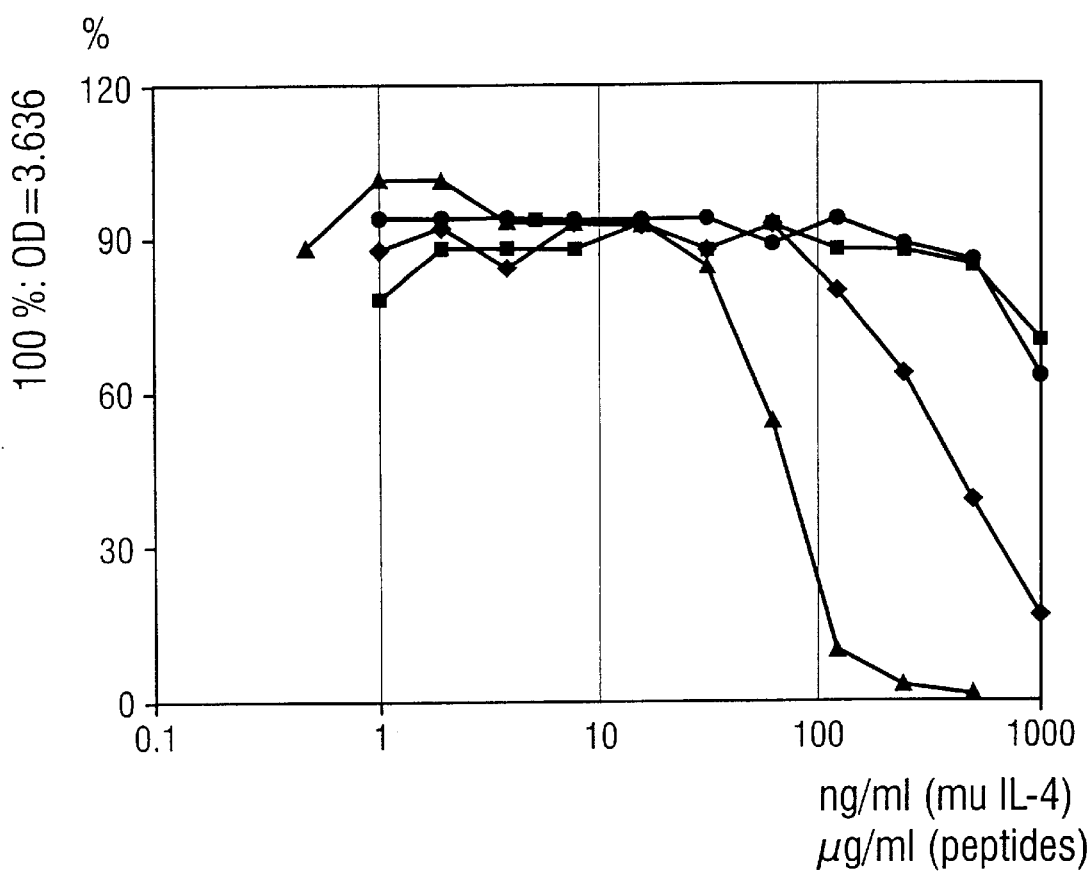
Figure 3:
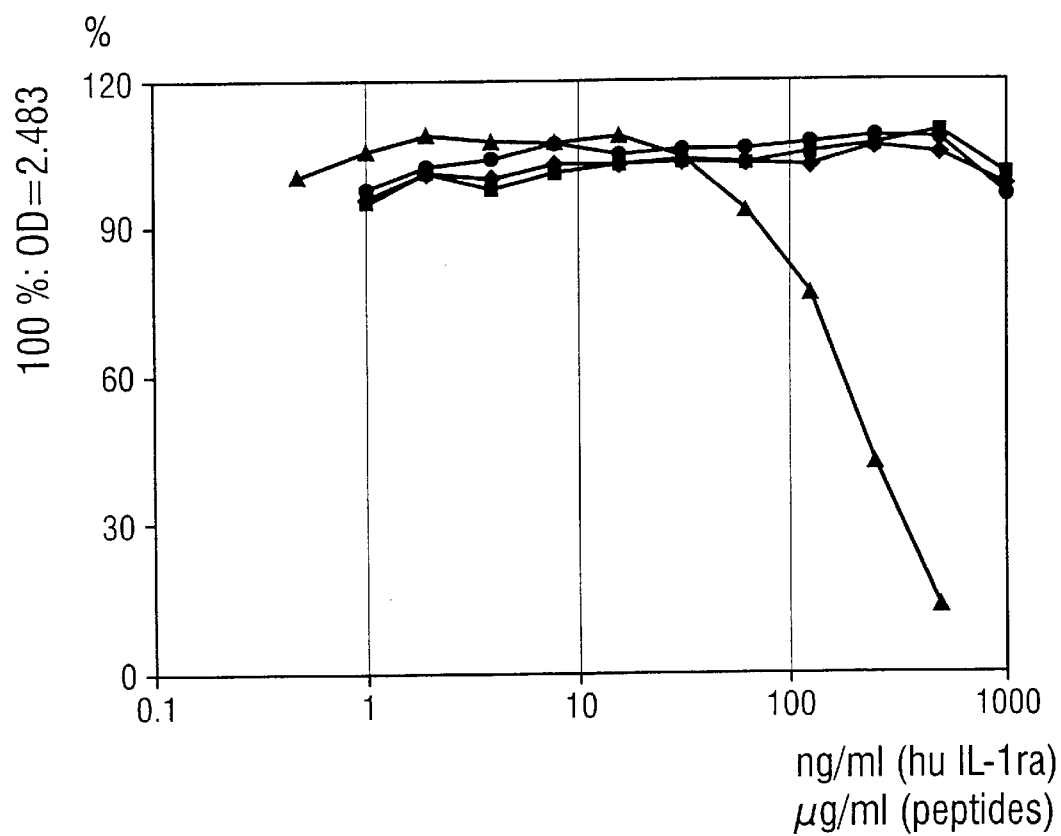

FIG. 1 shows that, in the huIL-4 binding test, unlabeled huIL-4 competes with biotinylated huIL-4 for binding to the human I-4 receptor. The same applies, in a corresponding manner, to muIL-4 and murine lL-4 receptor (FIG. 2) and for huIL-Ira and human IL-I receptor (FIG. 3). However, the peptide mixtures K 5993, K 0021 and K 0022 inhibit the binding of biotinylated huIL-4 and muIL-4 to their respective receptors (FIGS. 1 and 2) while they do not elicit any significant effect in the IL-Ira binding assay (FIG. 3).

The following IC$_{50}$ values were determined:

| | IC$_{50}$ [µg/ml] |
|---|---|
| cyclo(Val—Val—Xaa—Val—Val—(D)—Ala) | (K 5993) 37 |
| cyclo(val—Tyr—Xaa—Val—Tyr—(D)—Ala) | (K 0021) 68 |
| cyclo(Tyr—Val—Xaa—Tyr—Val—(D)—Ala) | (K 0022) 220 |
| cyclo(Val—Tyr—Ala—Val—Tyr—(D)—Ala) | 16.7 |
| cyclo(Tyr—Val—Ala—Tyr—Val—(D)—Ala) | 8.3 |
| cyclo(Tyr—Val—Hyp—Tyr—Val—(D)—Ala) | 17.4 |
| cyclo(Tyr—Val—Ile—Tyr—Val—(D)—Ala) | 62.5 |
| cyclo(Tyr—Val—Leu—Tyr—Val—(D)—Ala) | 41.3 |
| cyclo(Tyr—Val—Arg—Tyr—Val—(D)—Ala) | 96.6 |
| cyclo(Tyr—Val—Thr—Tyr—Val—(D)—Ala) | 92.0 |

Xaa - residue of a natural amino acid other than Cys or Trp

EXAMPLE 6
Effect on IL-4-induced Proliferation

The biological activity of the cyclohexapeptides of the formula I, or of their mixtures, was measured in a bioassay. IL-4 binds species-specifically to the IL-4 receptor. For this reason, a cell line was used which is of murine origin and which carries the murine IL-4 receptor in the cell membrane. This cell line was transfected with the complete gene for the human interleukin-4 receptor. This cell line functionally expresses murine and human membrane-located receptors simultaneously and the cell line proliferates both in dependence on murine and on human IL-4 (Nosley et al., *Cell*, 59, pp. 335–348 (Oct. 20, 1989, which is incorporated herein by reference). 1% DMSO was added to all the culture media in order to improve the solubility of the peptides.

a) Effect on Human IL-4-induced Proliferation

Figure 4A:
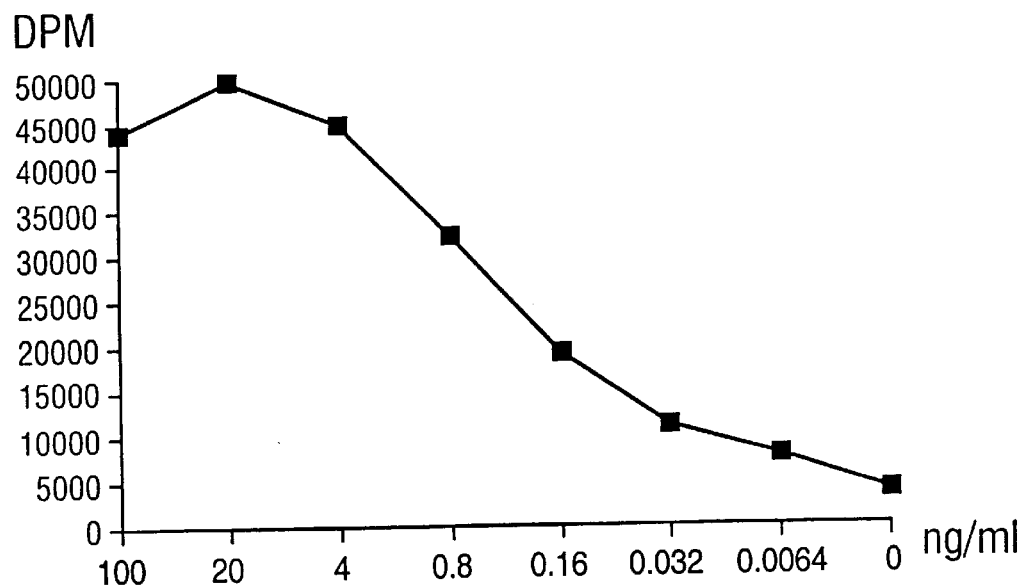
Figure 4B:
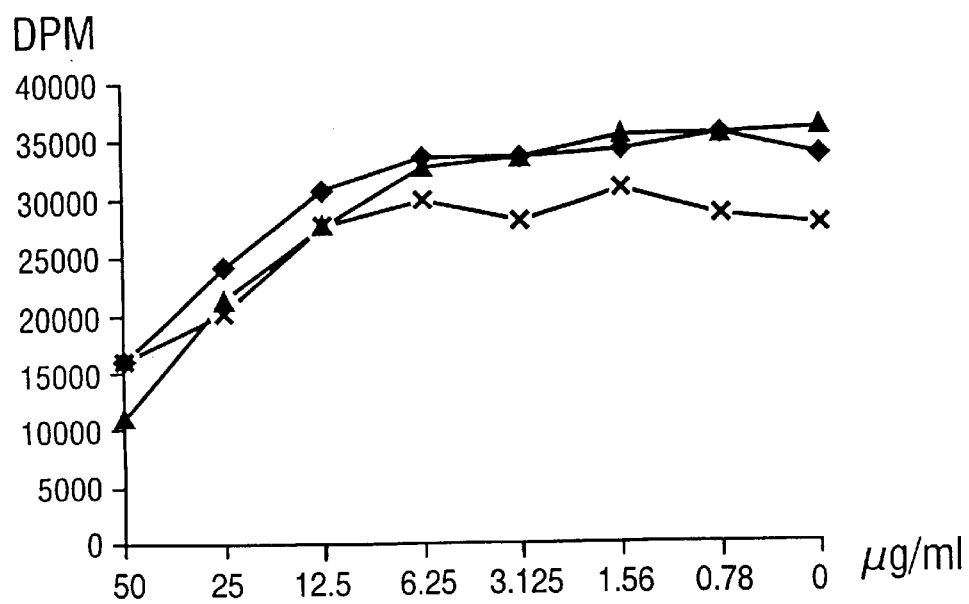

The cell line proliferates in dependence on human IL-4 (huIL-4), as depicted in FIG. 4 (standard curve). When a constant concentration of huIl-4 is used, each of the indicated peptide mixtures, which are titrated in individually, inhibits proliferation in a concentration-dependent manner (FIG. 4).

b) Effect on Murine IL-4-induced Proliferation

Figure 5A:
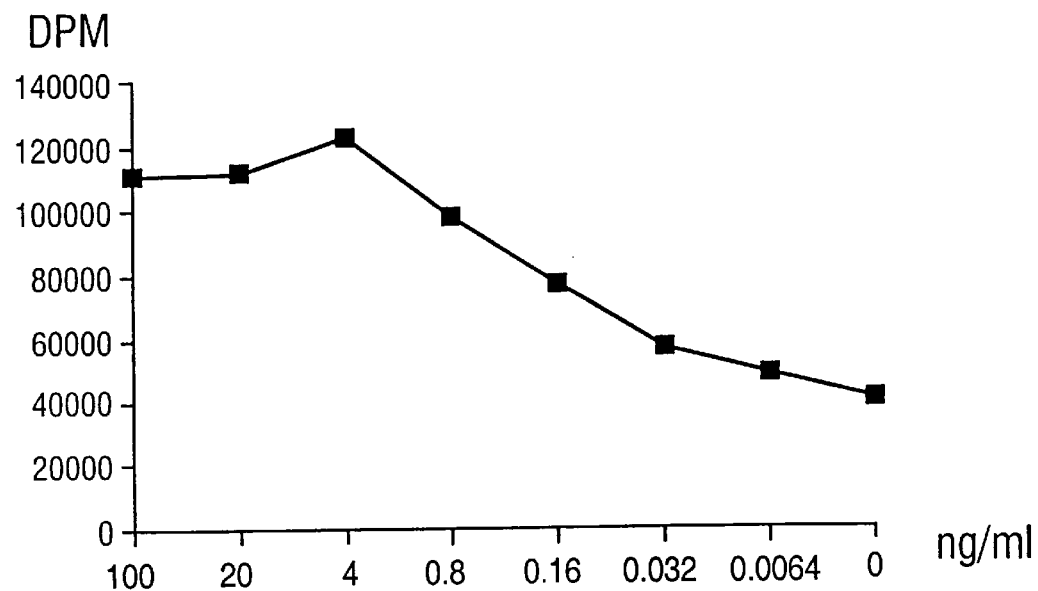
Figure 5B:
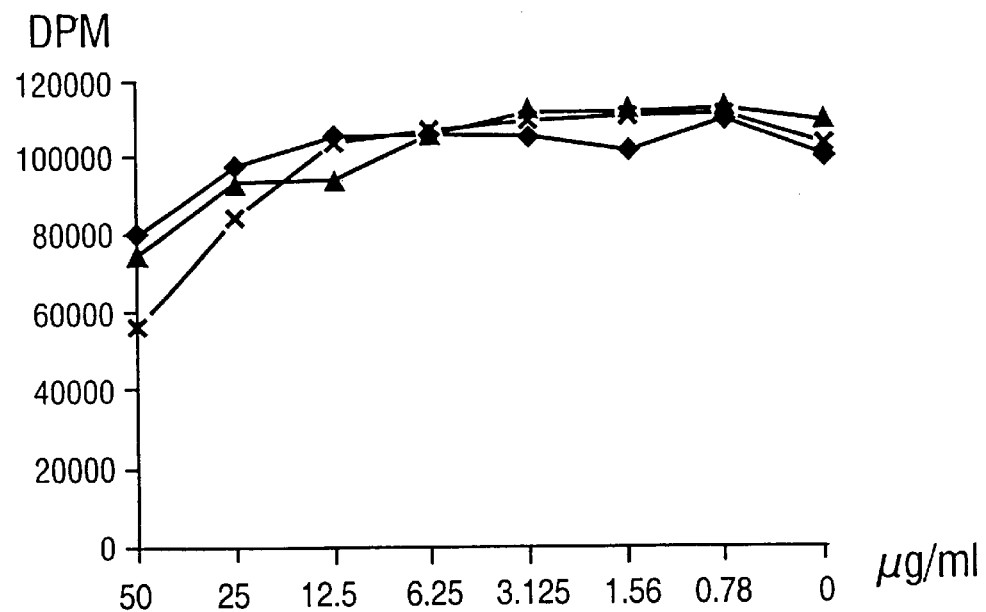

The cell line proliferates in dependence on murine IL-4 (muIL-4), as depicted in FIG. 5 (standard curve). When a constant concentration of muIL-4 is used, each of the indicated peptide mixtures, which are titrated in individually, inhibits proliferation in a concentration-dependent manner (FIG. 5).

EXAMPLE 7
Effect on IL-1-induced proliferation

Figure 6A:
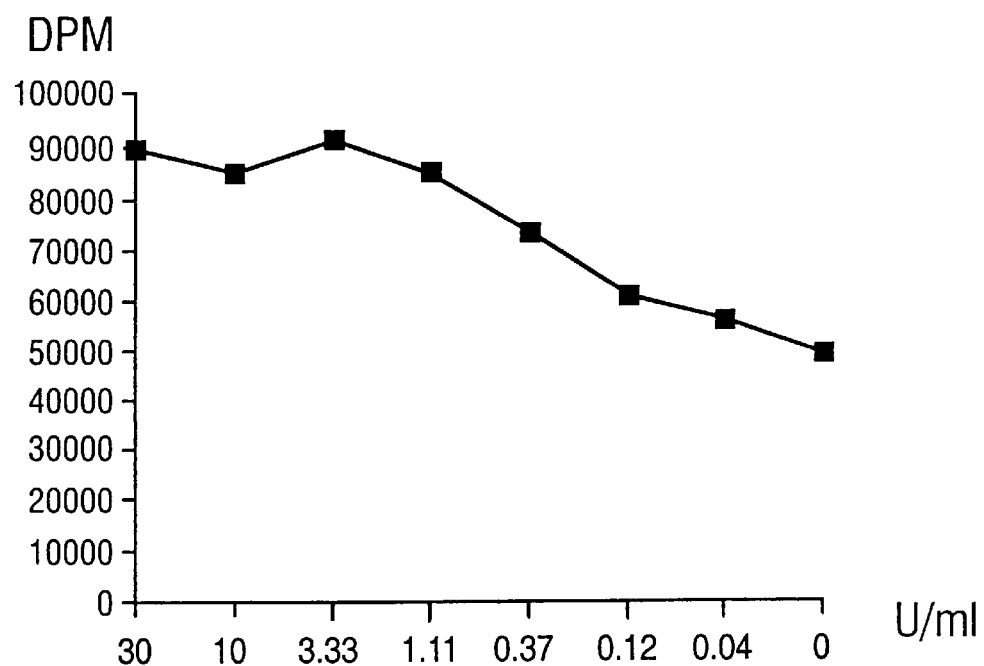
Figure 6B:
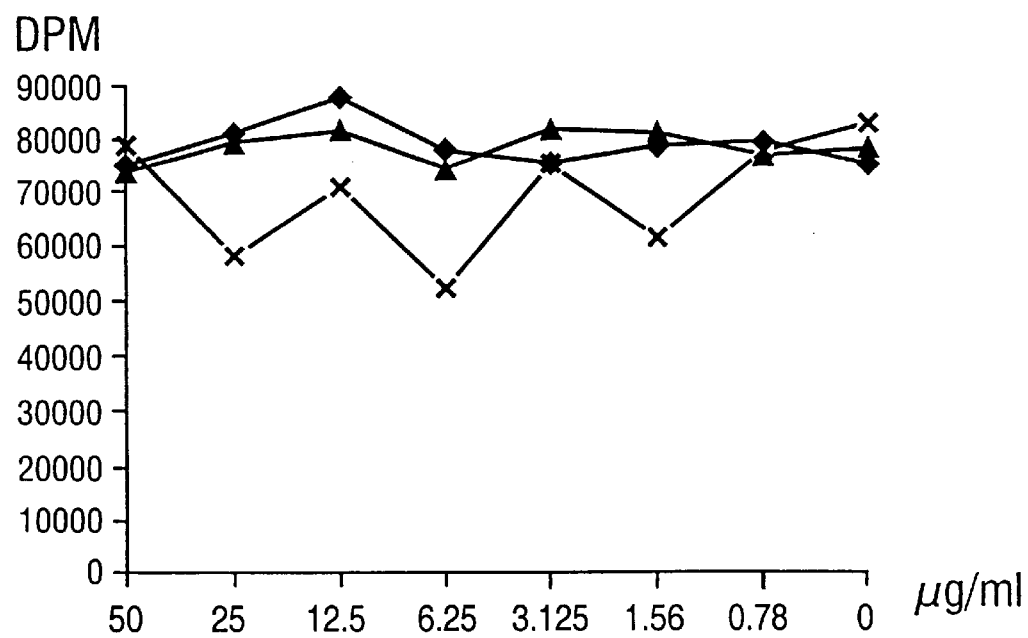

An IL-1-dependent T cell clone (D10(N4)M, Hopkins et al., *J. of Imm. Methods*, 120, pp. 271–276, (1989), which is incorporated hrein by reference) was used. 1% DMSO was added to the culture medium to improve the solubility of the peptides. The cells proliferate in dependence on human IL-I beta (huIL-I beta) (FIG. 6, standard curve). When a constant concentration of huIL-I beta is used, each of the indicated peptide mixtures, which are titrated in individually, fails to inhibit proliferation of the cell line, in the given concentration range (FIG. 6).

What is claimed is:

1. A cyclohexapeptide of the formula I cyclo(A-B-C-E-F-(D)-Ala)    (I)

in which
   A is the residue of an a-amino acid selected from Ala, Arg, Asp, Asn, Gln, Glu, Gly, His, Ile, Leu, Lys, Met, Phe, Pro, Thr, Tyr, and Val,
   B is the residue of an a-amino acid selected from Asp, Asn, Gln, Glu, His, Ile, Leu, Lys, Met, Phe, Pro, Ser, Thr, Tyr, and Val, and
   C, E and F are each independently the residue of an α-amino acid selected from Ala, Arg, Asp, Asn, Gln, Glu, Gly, His, Ile, Leu, Lys, Met, Phe, Pro, Ser, Thr, Tyr, and Val,
   or a physiologically tolerated salt thereof.

2. A cyclohexapeptide of the formula I or a physiologically tolerated salt thereof as claimed in claim 1, in which A and B are each independently the residue of an α-amino acid selected from Ile, Leu, Val, Phe and Tyr.

3. A pharmaceutical composition for the treatment or prophylaxis of an allergy or an infection comprising an effective amount of a cyclohexapeptide of the formula I or salt thereof as claimed in claim 2.

4. A diagnostic agent comprising a cyclohexapeptide of the formula I or salt thereof as claimed in claim 2.

5. A process for inhibiting the binding of interleukin-4 (IL-4) to the IL-4 receptor which comprises administering to a host in need of such inhibition an effective amount of a cyclohexapeptide of the formula or salt thereof as claimed in claim 2.

6. A process for preparing a pharmaceutical or diagnostic agent, which comprises mixing at least one cyclohexapeptide of the formula I or salt thereof as claimed in claim 2 with a physiologically acceptable excipient and, optionally, suitable additives and/or auxiliary substances.

7. A cyclohexapeptide of the formula I as claimed in claim 1, where the cyclohexapeptide is
   cyclo(Val-Val-C-Val-Val-(D)-Ala),
   cyclo(Val-Tyr-C-Val-Tyr-(D)-Ala) or
   cyclo(Tyr-Val-C-Tyr-Val-(D)-Ala)
      where C is the residue of an α-amino acid selected from
         Ala, Arg, Asp, Asn, Gln, Glu, Gly, His, Ile, Leu, Lys, Met, Phe, Pro, Ser, Thr, Tyr, and Val,
   or a physiologically tolerated salt thereof.

8. A pharmaceutical composition for the treatment or prophylaxis of an allergy or an infection comprising an effective amount of a cyclohexapeptide or salt thereof as claimed in claim 7.

9. A diagnostic agent comprising a cyclohexapeptide or salt thereof as claimed in claim 7.

10. A process for inhibiting the binding of interleukin-4 (IL-4) to the IL-4 receptor which comprises administering to a host in need of such inhibition an effective amount of a cyclohexapeptide or salt thereof as claimed in claim 1.

11. A process for preparing a pharmaceutical or diagnostic agent, which comprises mixing a cyclohexapeptide or salt thereof as claimed in claim 7 with a physiologically acceptable excipient and, optionally, suitable additives and/or auxiliary substances.

12. A process for preparing a cyclohexapeptide of the formula I or salt thereof as claimed in claim 1, which comprises:
   a) coupling suitable protected amino acid derivatives to a solid support,
   b) cleaving linear peptide which has been formed from the support while retaining any side-chain protective groups,
   c) cyclizing the linear peptide in solution, and
   d) eliminating any side-chain protective groups from the cyclized peptide.

13. A process for preparing a mixture of two or more cyclohexapeptides of the formula I or salts thereof as claimed in claim 1, which comprises
   a) coupling suitably protected amino acid derivatives in the form of a linear peptide to a solid support, and, for the purpose of introducing variable positions, either 1) adding a mixture of all chosen amino acids or
2) dividing the support, together with the linear peptides coupled to it, into fractions and coupling each fraction individually to a specific amino acid and then pooling the fractions once again, b) cleaving the mixture of linear peptides which has been formed from the support while retaining any protective groups, c) cyclizing the mixture of linear peptides in solution, and d) eliminating any protective group from the cyclized peptides and, optionally, e) converting the cyclized peptides into a physiologically tolerated salt.

14. A mixture prepared according to the process of claim 13.

15. A mixture comprising two or more cyclohexapeptides of the formula I or physiologically tolerated salts thereof as claimed in claim 1.

16. A pharmaceutical composition for the treatment or prophylaxis of an allergy or an infection comprising an effective amount of a mixture as claimed in claim 15.

17. A diagnostic agent comprising a mixture as claimed in claim 15.

18. A process for preparing a pharmaceutical or diagnostic agent, which comprises mixing a mixture as claimed in claim 15 with a physiologically acceptable excipient and, optionally, suitable additives and/or auxiliary substances.

19. A pharmaceutical composition for the treatment or prophylaxis of an allergy or an infection comprising an effective amount of a cyclohexapeptide of the formula I or a physiologically tolerated salt thereof as claimed in claim 1.

20. A diagnostic agent comprising a cyclohexapeptide of the formula I or physiologically tolerated salt thereof as claimed in claim 1.

21. A process for preparing a pharmaceutical or diagnostic agent, which comprises mixing at least one cyclohexapeptide the formula I or a physiologically tolerated salt thereof as claimed in claim 1 with a physiologically acceptable excipient and, optionally, suitable additives and/or auxiliary substances.

22. A cyclohexapeptide of the formula I as claimed in claim 1, where the cyclohexapeptide is
cyclo(Tyr-Val-Ala-Gly-F-(D)-Ala),
cyclo(Tyr-Val-Ala-Gln-F-(D)-Ala),
cyclo(Tyr-Val-Ala-Lys-F-(D)-Ala),
cyclo(Tyr-Val-Ala-Asn-F-(D)-Ala),
cyclo(Tyr-Val-Ala-Ile-F-(D)-Ala),
cyclo(Tyr-Val-Ala-Leu-F-(D)-Ala),
cyclo(Tyr-Val-Ala-Pro-F-(D)-Ala),
cyclo(Tyr-Val-Ala-Phe-F-(D)-Ala),
cyclo(Tyr-Val-Ala-His-F-(D)-Ala),
cyclo(Tyr-Val-Ala-Ala-F-(D)-Ala), or
cyclo(Tyr-Val-Ala-Tyr-F-(D)-Ala),
where F is the residue of an a-amino acid selected from Ala, Arg, Asp, Asn, Gln, Glu, Gly, His, Ile, Leu, Lys, Met, Phe, Pro, Ser, Thr, Tyr, and Val,
or a physiologically tolerated salt thereof.

23. A process for inhibiting the binding of interleukin-4 (IL-4) to the IL-4 receptor which comprises administering to a host in need of such inhibition an effective amount of a cyclohexapeptide of the formula I cyclo(A-B-C-E-F-(D)-Ala)  (I)

in which

A, B, C, E, and F are each independently the residue of an α-amino acid selected from Ala, Arg, Asp, Asn, Gln, Glu, Gly, His, Ile, Leu, Lys, Met, Phe, Pro, Ser, Thr, Tyr, and Val, or a physiologically tolerated salt thereof.

24. A process for inhibiting the binding of interleukin-4 (IL-4) to the IL-4 receptor which comprises administering to a host in need of such inhibition an effective amount of a mixture of two or more cyclohexapeptides of the formula I cyclo(A-B-C-E-F-(D)-Ala)  (I)

in which

A, B, C, E, and F are each independently the residue of an α-amino acid selected from Ala, Arg, Asp, Asn, Gln, Glu, Gly, His, Ile, Leu, Lys, Met, Phe, Pro, Ser, Thr, Tyr, and Val, or a physiologically tolerated salt thereof.

25. A method for the treatment or prophylaxis of an allergy or an infection comprising administering to a patient in need of such treatment, an effective amount of a cyclohexapeptide of the formula I cyclo(A-B-C-E-F-(D)-Ala)  (I)

in which

A, B, C, E, and F are each independently the residue of an a-amino acid selected from Ala, Arg, Asp, Asn, Gln, Glu, Gly, His, Ile, Leu, Lys, Met, Phe, Pro, Ser, Thr, Tyr, and Val, or a physiologically tolerated salt thereof.

26. A cyclohexapeptide of the formula I as claimed in claim 1, where the cyclohexapeptide is
cyclo(Val-Tyr-Ala-Val-Tyr-(D)-Ala),
cyclo(Yal-Tyr-Arg-Val-Tyr-(D)-Ala),
cyclo(Val-Tyr-Asn-Val-Tyr-(D)-Ala),
cyclo(Val-Tyr-Asp-Val-Tyr-(D)-Ala),
cyclo(Val-Tyr-Gln-Val-Tyr-(D)-Ala),
cyclo(Val-Tyr-Glu-Val-Tyr-(D)-Ala),
cyclo(Val-Tyr-Gly-Val-Tyr-(D)-Ala),
cyclo(Val-Tyr-His-Val-Tyr-(D)-Ala),
cyclo(Val-Tyr-Ile-Val-Tyr-(D)-Ala),
cyclo(Val-Tyr-Leu-Val-Tyr-(D)-Ala),
cyclo(Val-Tyr-Lys-Val-Tyr-(D)-Ala),
cyclo(Val-Tyr-Met-Val-Tyr-(D)-Ala),
cyclo(Val-Tyr-Phe-Val-Tyr-(D)-Ala),
cyclo(Val-Tyr-Pro-Val-Tyr-(D)-Ala),
cyclo(Val-Tyr-Ser-Val-Tyr-(D)-Ala),
cyclo(Val-Tyr-Thr-Val-Tyr-(D)-Ala),
cyclo(Val-Tyr-Tyr-Val-Tyr-(D)-Ala), or
cyclo(Val-Tyr-Val-Val-Tyr-(D)-Ala),
or a physiologically tolerated salt thereof.

27. A cyclohexapeptide of the formula I as claimed in claim 1, where the cyclohexapeptide is
cyclo(Tyr-Val-Ala-Tyr-Val-(D)-Ala),
cyclo(Tyr-Val-Gln-Tyr-Val-(D)-Ala),
cyclo(Tyr-Val-Lys-Tyr-Val-(D)-Ala),
cyclo(Tyr-Val-Glu-Tyr-Val-(D)-Ala,
cyclo(Tyr-Val-Asp-Tyr-Val-(D)-Ala),
cyclo(Tyr-Val-Phe-Tyr-Val-(D)-Ala),
cyclo(Tyr-Val-Gly-Tyr-Val-(D)-Ala),
cyclo(Tyr-Val-His-Tyr-Val-(D)-Ala), cyclo(Tyr-Val-Ile-Tyr-Val-(D)-Ala),
cyclo(Tyr-Val-Leu-Tyr-Val-(D)-Ala),
cyclo(Tyr-Val-Asn-Tyr-Val-(D)-Ala),
cyclo(Tyr-Val-Pro-Tyr-Val-(D)-Ala),
cyclo(Tyr-Val-Arg-Tyr-Val-(D)-Ala),
cyclo(Tyr-Val-Ser-Tyr-Val-(D)-Ala),
cyclo(Tyr-Val-Thr-Tyr-Val-(D)-Ala),
cyclo(Tyr-Val-Val-Tyr-Val-(D)-Ala),
cyclo(Tyr-Val-Tyr-Tyr-Val-(D)-Ala), or
cyclo(Tyr-Val-Met-Tyr-Val-(D)-Ala), or a physiologically tolerated salt thereof.

* * * * *

UNITED STATES PATENT AND TRADEMARK OFFICE
CERTIFICATE OF CORRECTION

PATENT NO.: 5,869,447

DATED: February 9, 1999

INVENTORS: Stephan HENKE et al.

It is certified that an error appears in the above-identified patent and that said Letters Patent is hereby corrected as shown below:

Claim 1, Column 11, line 62, "a-amino" should read --α-amino--.

Claim 1, Column 11, line 65, "a-amino" should read --α-amino--.

Claim 5, Column 12, line 19, after "formula", insert --I--.

Claim 21, Column 13, line 38, before "the formula I", insert --of--.

Claim 21, Column 13, line 39, after "claim 1", insert --,--.

Claim 22, Column 13, line 56, "a-amino" should read --α-amino--.

Claim 25, Column 14, line 28, "a-amino" should read --α-amino--.

Claim 26, Column 14, line 36, "Yal" should read --Val--.

Signed and Sealed this

Twelfth Day of September, 2000

Q. TODD DICKINSON

*Attest:*

*Attesting Officer*      *Director of Patents and Trademarks*